United States Patent [19]

Dutton et al.

[11] Patent Number: 5,026,643

[45] Date of Patent: Jun. 25, 1991

[54] FERMENTATION PROCESS FOR THE PREPARATION OF NOVEL C.25 (SUBSTITUTED(2-PROPENYL) MILBEMYCINS

[75] Inventors: Christopher J. Dutton; David A. Perry, both of New York, N.Y.

[73] Assignee: Pfizer Inc., New York, N.Y.

[21] Appl. No.: 485,397

[22] Filed: Feb. 26, 1990

Related U.S. Application Data

[60] Division of Ser. No. 382,016, Jul. 18, 1989, Pat. No. 4,927,847, which is a continuation of Ser. No. 227,921, Aug. 3, 1988, abandoned.

[30] Foreign Application Priority Data

Sep. 15, 1987 [GB] United Kingdom ................ 8721647

[51] Int. Cl.$^5$ ..................... C12R 1/465; C12P 17/18; A61K 31/37
[52] U.S. Cl. ..................................... 435/119; 435/886
[58] Field of Search ............................... 435/119, 886

[56] References Cited

U.S. PATENT DOCUMENTS

| | | | |
|---|---|---|---|
| 4,696,922 | 9/1987 | Sturm et al. | 514/185 |
| 4,927,847 | 5/1990 | Dutton et al. | 514/450 |
| 4,929,638 | 5/1990 | Dutton et al. | 514/450 |

FOREIGN PATENT DOCUMENTS

| | | |
|---|---|---|
| 0170006 | 6/1986 | European Pat. Off. |
| 0214731 | 3/1987 | European Pat. Off. |
| 300674 | 1/1989 | European Pat. Off. |
| 2166436 | 5/1986 | United Kingdom |
| 2167751 | 6/1986 | United Kingdom |
| 2176182 | 12/1986 | United Kingdom |

*Primary Examiner*—Herbert J. Lilling
*Attorney, Agent, or Firm*—Peter C. Richardson; J. Trevor Lumb; Gregg C. Benson

[57] ABSTRACT

Antiparasitic milbemycin derivatives having at the C.25 position a substituted 2-propenyl group —C(CH$_3$)=CH—R$^2$ wherein R$^2$ is a C$_3$–C$_8$ alkyl, alkenyl or alkynyl group which may optionally contain an oxygen or sulphur atom as part of the chain, or a C$_3$–C$_8$ cycloalkyl or cycloalkenyl group, or a 3 to 6 membered oxygen or sulphur containing heterocyclic ring which may optionally be substituted by one or more alkyl groups or halogen atoms; and process for their preparation.

2 Claims, No Drawings

FERMENTATION PROCESS FOR THE PREPARATION OF NOVEL C.25 (SUBSTITUTED(2-PROPENYL) MILBEMYCINS

CROSS REFERENCE TO RELATED APPLICATIONS

This is a divisional application of application Ser. No. 07/382,016, filed July 18, 1989, now U.S. Pat. No. 4,927,847, which is a continuation of application Ser. No. 07/227,921, filed Aug. 3, 1988, now abandoned.

This invention relates to antiparasitic agents and in particular to compounds related to the milbemycins but having a novel substituent at the 25-position and to a process for their preparation.

The milbemycins are a group of broad spectrum antiparasitic agents related to the avermectins but differing from them in lacking the sugar residues at the 13-position. This invention relates specifically to the subgroup of milbemycins which are characterised by the unsaturation present in the 25-position substituent produced by fermenting strains of the microorganisms *Streptomyces cyaneogriseus ssp noncyanogenus* NRRL 15773 or *Streptomyces thermoarchaensis* NCIB 12015. The morphological and cultural properties of the strains NRRL 15773 and NCIB 12015 are described in detail in the European Patent Application No. 0170006 and UK Patent Application No. GB 2 166 436A respectively. The first of these patent applications describes the isolation and characterisation of thirteen individual milbemycins designated LL-F28249α-ν and the second describes a complex of six components designated S541 Factors A-F.

According to the specification of our European patent application No. 0214731, published Mar. 18, 1987, we describe a process for preparing novel avermectins having a modified group at the 25-position, by adding a carboxylic acid or derivative thereof to a fermentation of an avermectin producing organism.

We have now discovered that by adding certain specified carboxylic acids, or derivatives thereof, to a fermentation of the above milbemycin producing organisms it is possible to obtain novel compounds, related to the complexes LL-F28249 and S541, but having an unnatural substituent group at the 25-position.

Surprisingly, however, the group is not directly attached to the 25-position, as in the avermectins, but is linked via a 2-propenyl group.

The novel compounds are highly active antiparasitic agents having particular utility as anthelmintics, ectoparasiticides, insecticides and acaricides.

Conventional chemical transformation reactions can be used to prepare further derivatives from these compounds. Thus, according to the invention, there are provided compounds having the formula (I):

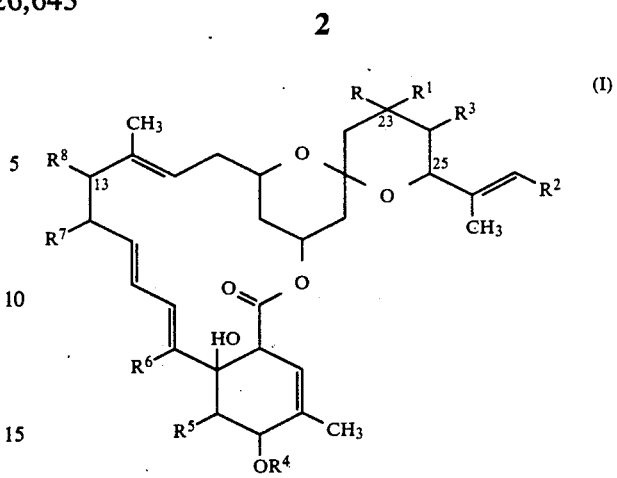

wherein either R is hydrogen and $R^1$ is hydroxy or R and $R^1$ are taken together and are oxo;

$R^2$ is a $C_3$–$C_8$ straight or branched-chain alkyl, alkenyl or alkynyl group which may optionally contain an oxygen or sulphur atom as part of the chain, or a $C_3$–$C_8$ cycloalkyl or cycloalkenyl group, or a 3 to 6 membered oxygen or sulphur containing heterocyclic ring which may be saturated or fully or partially unsaturated and which may optionally be substituted by one or more $C_1$–$C_4$ alkyl groups or halogen atoms;

$R^3$ is methyl or ethyl;

$R^4$ is hydrogen or methyl;

either $R^5$ is hydrogen or hydroxy and $R^6$ is methyl or hydroxymethyl, or the two groups $R^5$ and $R^6$ are taken together and are —O—$CH_2$—;

$R^7$ is hydrogen, methyl or ethyl; and $R^8$ is hydrogen or halogen;

with the proviso that when $R^2$ is branched chain alkyl it is not isopropyl.

In the above definition halogen means fluorine, chlorine, bromine or iodine.

A preferred class of compounds have the formula (II):

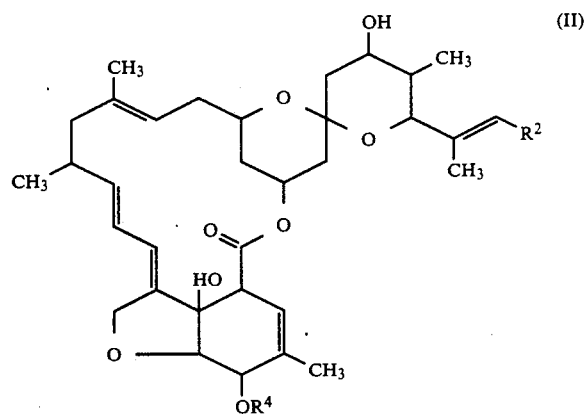

wherein $R^2$ and $R^4$ are as previously defined.

Particularly preferred are compounds of the formula (II) wherein $R^2$ is (1-methylthio)ethyl, 2-pent-4-enyl or 2-butyl.

In accordance with the invention, compounds of the formula (I) wherein $R^8$ is hydrogen are prepared by fermenting a strain of the milbemycin producing organism *Streptomyces cyaneogriseus* subsp. *noncyanogenus* NRRL 15773 or *Streptomyces thermoarchaensis* NCIB 12015 in the presence of the appropriate carboxylic acid of the formula $R^2CO_2H$, wherein $R^2$ is as previously defined, or a salt, ester or amide thereof, or oxidative precursor therefor.

The acid is added to the fermentation either at the time of inoculation or at intervals during the fermentation. Production of the compounds of formula (I) may be monitored by removing samples from the fermentation, extracting with an organic solvent and following the appearance of the compound of formula (I) by chromatography, for example using high pressure liquid chromatography. Incubation is continued until the yield of the compound of formula (I) has been maximised, generally for a period of from 4 to 6 days.

A preferred level of each addition of the carboxylic acid or derivative thereof is between 0.05 and 10 grams per liter. The best yields of the compounds of formula (I) are obtained by gradually adding the acid to the fermentation, for example by daily additions of the acid or derivative thereof over a period of several days. The acid is preferably added as a salt, such as the sodium or ammonium salt, but may be added as an ester, such as the methyl or ethyl ester or as an amide. Alternative substrates which may be used in the fermentation are derivatives which are oxidative precursors for the carboxylic acids; thus, for example suitable substrates would be aminoacids of the formula $R^2CH(NH_2)CO_2H$, glyoxylic acids of the formula $R^2COCO_2H$, methylamine derivatives of the formula $R^2CH_2NH_2$, substituted lower alkanoic acids of the formula $R^2(CH_2)_nCO_2H$ wherein n is 2, 4 or 6, methanol derivatives of the formula $R^2CH_2OH$ or aldehydes of the formula $R^2CHO$, wherein $R^2$ is as previously defined. The media used for the fermentation may be a conventional complex media containing assimilable sources of carbon, nitrogen and other trace elements.

After fermentation for a period of several days at a temperature preferably in the range of from 24° to 33° C., the fermentation broth is centrifuged or filtered and the mycelial cake is extracted with acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product containing the compounds of formula (I) is further purified as necessary by chromatography, for example using preparative reverse phase, high pressure liquid chromatography.

The product is generally obtained as a mixture of the compounds of formula (I) wherein R, $R^1$, $R^3$, $R^4$, $R^5$, $R^6$ and $R^7$ are as previously defined and, $R^8$ is H; however the proportions of the various components can vary depending on the particular organism used, the carboxylic acid employed and the conditions used.

We have found that a broad range of carboxylic acids as defined by $R^2CO_2H$ may be added to the fermentation to yield milbemycin derivatives having a novel substituent at the 25-position. Examples of particular acids which may be employed include the following:
2-methylpent-4-enoic acid
2-methylbutyric acid
2-methylthiopropionic acid.

In one particular and preferred aspect of the invention the fermentation is performed in the presence of 2-methylthiopropionic acid sodium salt to yield predominantly the compounds of formula (II) wherein $R^2$ is (1-methylthio)ethyl and $R^4$ is H.

In another preferred aspect of the invention the fermentation is performed in the presence of 2-methylbutyric acid sodium salt to yield predominantly the compound of formula (II) wherein $R^2$ is 2-butyl and $R^4$ is H or methyl.

In a further preferred aspect of the invention the fermentation is performed in the presence of 2-methylpent-4-enoic acid sodium salt to yield predominantly the compound of formula (II) wherein $R^2$ is 2-pent-4-enyl and $R^4$ is H.

Compounds of the formula (I) wherein $R^8$ is H may be converted to the corresponding compounds wherein $R^8$ is halogen using published procedures. The reaction is performed by first protecting the hydroxyl groups present at the 5, 6, 8a and 23 positions, for example as the t-butyldimethylsilyloxy acetyl derivative, followed by halogenation at the 13 position using for example N-bromosuccinimide in the presence of light followed by deprotection. Alternatively the process is performed by epoxidation of the 14, 15 double bond using a peracid, for example m-chloroperbenzoic acid. The hydroxyl groups present at the 5, 6, 8a and 23 positions are protected, for example as the t-butyldimethylsilyl derivative, and the compound is treated with a pre-formed complex of hydrazoic acid ($HN_3$) and triethylaluminium in an inert solvent to give the 15-hydroxy-$\Delta^{13,14}$-milbemycin derivative. This compound is then converted to the 13-halogeno-milbemycin by treatment with an appropriate halogenating reagent, for example phosphorus tribromide, to give the 13-bromo derivative. These steps together with appropriate reagents and reaction conditions are described in the European patent application No. 0184989.

The halo-compounds, as well as being active antiparasitic agents, can serve as intermediates for preparation of the corresponding avermectin derivatives. Thus the protected halo-derivative is converted to the 13-acetoxy derivative by treatment with a mixture of sodium acetate in acetic acid. Subsequent reaction with sodium hydroxide gives the 13-hydroxy milbemycin to which the L-oleandrosyl-α-L-oleandrosyloxy group may be attached by reaction with an acetohalo derivative of the disaccharide. The product is then finally deprotected to give the avermectin. These steps together with appropriate reagents and reaction conditions are described in U.S. Pat. No. 4,093,629 and British patent No. 1579118. Certain of the avermectin products produced by this procedure are novel compounds, not previously obtainable.

The compounds of formula (I) wherein R and $R^1$ are taken together and are oxo may be isolated from the mixture of products obtained in the fermentation of the organism *Streptomyces thermoarchaensis* NCIB 12015 or of a mutant thereof as described in British patent application No. GB 2176182A, or they may be obtained by oxidation of the corresponding compounds of formula (I) wherein R is H and $R^1$ is OH. Appropriate reagents and procedures for performing the oxidation are described in GB No. 2176182A.

The compounds of formula I wherein $R^4$ is H may also be prepared from the corresponding compounds wherein $R^4$ is $CH_3$ by demethylation. This reaction is achieved by treating the 5-methoxy compound, or a suitably protected derivative thereof, with mercuric acetate and hydrolysing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209.

The compounds of the invention are highly active antiparasitic agents having particular utility as anthelmintics, ectoparasiticides, insecticides and acaricides.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars, fire ants, termites and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or preferably a liquid drench, or alternatively, they may be administered by injection or as an implant. Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. A drench formulation may be prepared by dispersing the active ingredient in an aqueous solution together with dispersing or wetting agents etc. and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

For human use the compounds are administered as a pharmaceutically acceptable formulation in accordance with standard medical practice.

This invention is illustrated by the following Examples in which Examples 1–7 are Examples of the preparation of compounds of the formula (I) and Examples 8 and 9 illustrate the antiparasitic and insecticidal activity of the compounds. The designations milbemycin $A_3$ and milbemycin $B_2$ refer to the natural milbemycins (Antibiotic B-41) of formula (II) but lacking the hydroxyl group at the 23-position and with methyl at the 25-position wherein $R^4$ is hydrogen or methyl respectively.

EXAMPLE 1

23-Hydroxy-25-desmethyl-25-(1-methyl-3-methylthio-but-1-enyl)milbemycin $A_3$ (formula II; $R^4=H$, $R^2=CH_3CH(SCH_3)-$)

A frozen mycelial preparation of *S. cyaneogriseus* subsp. *noncyanogenus* NRRL 15773 was inoculated into 50 mls of medium containing glucose (1 g), distillers solubles (0.75 g) and yeast extract (0.25 g) and incubated at 28° C. for 2 days with agitation. This culture was used to inoculate a three liter flask containing 600 mls of the same medium which was incubated as above for a further two days. This culture (100 mls.) was used to inoculate 2.5 liters of medium of the following composition, contained in a 5 liter fermenter:

Glucose (68.5 g), Trusoy flour (31.25 g), cane molasses (3.75 g), dipotassium hydrogen phosphate (0.375 g), calcium carbonate (3.125 g), and N-morpholinopropane sulphonic acid (25 g). The fermentation was incubated at 28° C. with agitation at 1200 rpm and aeration of 2.5 liters per minute.

2-Methylthiopropionic acid (1 g) was added after 24 hours incubation and the fermentation was continued for a further 120 hours. The mycelium was removed by filtration and extracted with acetone (1.5 liters) followed by methylene chloride (1.5 liters).

The methylene chloride extracts from six fermentations as described above were combined and concentrated to dryness to give the crude product as a dark gum. This material was dissolved in a mixture of methylene chloride and hexane (1:4) and added to a column of basic alumina (160 g). The column was eluted with 400 ml of solvent of the same composition. The column was then eluted with methanol collecting 100 ml fractions. Fractions 1–4 were combined and concentrated to yield partially purified material (15.8 g) as a yellow oil. This oil was partitioned between isooctane (100 ml) and methanol (50 ml). The methanol layer was separated and water (100 ml) added. This mixture was extracted with methylene chloride (2×50 ml) and the lower layer was dried with anhydrous sodium sulphate and evaporated to give partially purified product as an oil (10 g). This material was dissolved in a mixture of methylene chloride and ethyl acetate (3:1) and added to a column of silica (250 g). The column was eluted with a solvent of the same composition and 50 ml fractions were collected. The fractions containing the desired product were identified by analytical HPLC, combined and concentrated to give the semipurified milbemycin derivative. A sample of this material (150 mg) was further purified by chromatography on a C18 Zorbax ODS (Trademark, Dupont) column (21 mm×25 cm) eluting with a mixture of methanol and water (78:22) at a flow rate of 9 mls. per minute. Fractions collected at around 70 minutes were combined and the solvent was evaporated to yield the compound of formula (II) wherein $R^2$ is (1-methylthio)ethyl and $R^4$ is H, as a white powder, m.p. 120°–122° C. The structure of the product was confirmed by mass spectrometry and by C13 nuclear magnetic resonance spectroscopy as follows:

Fast atom bombardment mass spectrometry was performed on a VG model 7070E mass spectrometer using a sample matrix of glycerol, thioglycerol, water and sodium chloride. (M+Na+) observed at m/e 667 (theoretical 667).

Electron impact mass spectrometry was performed using a VG model 7070F mass spectrometer. The m/e values for the principal fragments were 644 (M+), 626, 608, 579, 561, 498, 480, 450, 354, 315, 185, 151.

The C13 nuclear magnetic resonance spectral data were obtained on a Nicolet QE 300 spectrometer with a sample concentration of 20 mg/ml in deuterochloroform. The chemical shifts in parts per million relative to tetramethylsilane were 11.6, 14.0 (two unresolved signals), 15.6, 19.9, 20.8, 22.3, 34.8, 35.9, 36.0, 36.2, 38.4, 40.8, 41.2, 45,8, 48.5, 67.7 (two unresolved signals), 68.5, 68.7, 69.1, 76.6, 79.3, 80.3, 99.8, 118.0, 120.2, 120.4, 123.4, 132.6, 134.1, 137.4, 138.0, 139.5, 142.8, 173.4.

EXAMPLE 2

23-Hydroxy-25-desmethyl-25-(1,3-dimethylpent-1-enyl)milbemycin $A_3$ (formula (II, $R^4$=H, $R^2$=CH$_3$CH$_2$CH(CH$_3$)—)

The conditions of Example 1 were followed except that 2-methylbutyric acid was used as substrate. The methylene chloride extract derived from twelve 2.5 liter fermentations was evaporated to give a brown oil (27.2 g) which was partially purified by dissolving in a mixture of dichloromethane and ethyl acetate (4:1) and adding to a column of silica (250 g). The column was eluted with solvent of the same composition and 50 ml fractions were collected. The combined fractions 4 and 5 were used in Example 3 and the fractions 7–11 containing the title compound (identified by thin layer chromatography) were combined and evaporated to give the semi-purified milbemycin derivative (2.73 g). This material was further purified by chromatography on a Dynamax 60-A C-18 (Trademark, Rainin) column (41×250 mm) eluting with a mixture of water and methanol (1:4). Final purification was achieved by chromatography on a C18 Zorbax ODS (Trademark, Dupont) column (21 mm×25 cm) eluting with a mixture of water and methanol (1:4) at a flow rate of 9 mls. per minute. Fractions collected at around 90 minutes were combined and the solvent was evaporated to yield the title compound of formula (II) wherein $R^2$ is 2-butyl and $R^4$ is H, as a white powder having a melting point of 125°–128° C. The structure of the product was confirmed by mass spectrometry and by C13 and proton nuclear magnetic resonance spectroscopy as follows:

Fast atom bombardment mass spectrometry was performed on a VG model 7070E mass spectrometer using a sample matrix of glycerol, thioglycerol, water and sodium chloride. (M+Na+) observed at m/e 649 (theoretical 649).

Electron impact mass spectrometry was performed using a VG model 7070F mass spectrometer. The m/e values for the principal fragments were 626 (M+), 608, 590, 480, 462, 425, 354, 314, 248, 151.

The C13 nuclear magnetic resonance spectral data were obtained on a Nicolet QE 300 spectrometer with a sample concentration of 20 mg/ml in deuterochloroform. The chemical shifts in parts per million relative to tetramethylsilane were 11.5, 12.1, 14.1, 15.7, 20.1, 20.4, 22.4, 30.2, 33.8, 34.9, 36.1, 36.2, 36.3, 40.9, 41.3, 45.8, 48.6, 67.8, 67.9, 68.6, 68.6, 69.5, 76.8, 79.4, 80.3, 99.9, 118.2, 120.4, 123.5, 131.6, 136.2, 137.5, 138.0, 139.5, 142.9, 173.5.

The proton magnetic resonance spectral data were obtained on a Nicolet QE 300 spectrometer with the sample in deuterochloroform solution. The chemical shifts of characteristic signals in parts per million relative to tetramethylsilane were 5.85–5.7 (m, 2H), 5.45 (bs, 1H), 5.45–5.25 (m, 2H), 5.20 (d, 1H), 4.98 (m, 1H), 4.70 (m, 2H), 4.32 (t, 1H), 3.99 (d, 1H), 3.90 (s, 1H), 3.80 (d, 1H), 3.61 (d, 1H), 3.30 (m, 1H), 1.90 (bs, 3H), 1.64 (s, 3H), 1.56 (s, 3H), 1.03 (d, 3H), 0.84 (d, 3H).

EXAMPLE 3

23-Hydroxy-25-desmethyl-25-(1,3-dimethylpent-1-enyl)milbemycin $B_2$ (formula II, $R^4$=CH$_3$, $R^2$=CH$_3$CH$_2$CH(CH$_3$)—)

The combined fractions 4 and 5 from Example 2 were evaporated to dryness to give 2.25 g of residue which was further purified in two equal portions by chromatography on a Dynamax 60-A C-18 (Trademark, Rainin) column (41×250 mm) eluting with a mixture of methanol and water (85:15) at a flow rate of 45 mls per minute. Fractions eluting at around 70 minutes containing the title compound were combined and the solvent evaporated to give the semi-purified milbemycin. This material was further purified by column chromatography on silica gel, eluting with a mixture of dichloromethane and ethyl acetate (4:1) and finally purified by high pressure liquid chromatography using an Ultrasphere-ODS (Trademark, Beckman) column (10×250 mm) eluting with a mixture of methanol and water (72:28) at a flow rate of 4 mls per minute. Fractions eluting at around 70 minutes contained the pure title compound and were evaporated to dryness. The structure of the product was confirmed by fast atom bombardment mass spectrometry performed on a VG model 7070E mass spectrometer using a sample matrix of trigol, tetragol, water and sodium chloride. (M+Na+) observed at m/e 663 (theoretical 663).

EXAMPLE 4

23-Hydroxy-25-desmethyl-25(1,3-dimethyl-hexa-1,5-dienyl)milbemycin $A_3$ (formula II, $R^4$=H, $R^2$=CH$_2$=CHCH$_2$CH(CH$_3$)—)

The conditions of Example 1 were followed except that 2-methylpent-4-enoic acid was used as substrate. The crude extract derived from twelve 2.5 liter fermentations (30 g) was partially purified by column chromatography using alumina (active, neutral, Brockmann grade 1, BDH Chemicals Ltd., 500 g) eluting initially with hexane and then a mixture of dichloromethane and methanol (1:1), collecting 200–250 ml fractions. The fractions were analysed by t.l.c. and those containing the desired product were combined and evaporated under vacuum. A portion of this material (10 g) was further purified by column chromatography using silica gel (Kieselgel 60, 230–400 mesh, Merck, 500 g) eluting with a mixture of dichloromethane and ethyl acetate (4:1). Fractions containing the desired product were combined and evaporated under vacuum. This material was further purified in batches by HPLC using a Dynamax 60-A C-18 (Trademark, Rainin) column (41×250 mm) eluting with a mixture of methanol and water (4:1) at a flow rate of 52 ml per minute. Fractions were analysed by HPLC using an Ultrasphere-ODS (5 μm) (Trademark—Beckman) column (10×250 mm) eluting with a methanol-water gradient and those fractions containing the title compound were combined and evaporated under vacuum. Final purification was achieved by chromatography using an Ultrasphere-ODS (5 μm) (Trademark—Beckman) HPLC column (10×250 mm) eluting with a mixture of water and methanol (18:82) at a flow rate of 3 ml per minute. Fractions containing the pure title compound were combined and evaporated to dryness under vacuum. The structure of the product was confirmed by mass spectrometry and by proton nuclear magnetic resonance spectroscopy as follows:

Fast atom bombardment mass spectrometry was performed on a VG model 7070E mass spectrometer using a sample matrix of glycerol, thioglycerol, water and sodium chloride. $(M+Na^+)$ observed at m/e 661 (theoretical 661).

Electron impact mass spectrometry was performed using a VG model 7070F mass spectrometer. The m/e values for the principal fragments were 620 $(M-H_2O)^+$, 602 $(M-2H_2O)^+$, 492, 470, 442, 425.

The proton magnetic resonance spectral data were obtained on a Nicolet QE 300 spectrometer with the sample in deuterochloroform solution. The chemical shifts of characteristic signals in parts per million relative to tetramethylsilane were 5.95–5.70 (3H, m), 5.45 (bs, 1H), 5.4–5.27 (m, 2H), 5.23 (d, 1H), 5.10 (d, 1H), 5.05 (bs, 1H), 4.98 (m, 1H), 4.70 (m, 2H), 4.31 (t, 1H), 4.00 (d, 1H), 3.9–3.8 (m, 2H), 3.8 (d, 1H), 3.7–3.6 (m, 1H), 3.60 (d, 1H), 3.3 (m, 1H), 1.90 (bs, 3H), 1.65 (s, 3H), 1.57 (s, 3H), 1.43 (t, 1H), 1.03 (d, 3H), 0.98 (d, 3H), 0.83 (d, 3H).

EXAMPLE 5

23-Hydroxy-25-desmethyl-25(1,3-dimethyl-hexa-1,5-dienyl)milbemycin $A_3$ (formula II, $R^4=H$, $R^2=CH_2=CHCH_2CH(CH_3)-$)

An inoculum of Streptomyces thermoarchaensis NCIB 12015 was prepared by washing with sterile water (10 ml) a slant culture which was maintained on a medium prepared from yeast extract (0.5 g), malt extract (30 g), peptone (5 g) and agar (20 g) in tap water (1 liter adjusted to pH 5.4. This inoculum was trasnferred to an Erlenmeyer flask containing 50 ml of a medium containing glucose (0.8 g), glycerol (0.8 g), peptone (0.8 g), NaCl (0.06 g), $CaCO_3$ (0.02 g) in tap water adjusted to pH 7. The flask was incubated at 28° C. on a rotary shaker operating at 170 rpm for 48 hours. The resultant vegetative growth was transferred to a 3 liter mechanically agitated vessel containing glucose (5 g), dextrin (50 g), Trusoy flour (25 g), cane molasses (3 g), $K_2HPO_4$ (0.25 g), $CaCO_3$ (2.5 g) and 3-(N-morpholino)propanesulphonic acid (42.0 g) in tap water (2 liters) adjusted to pH 6.5 by addition of 1N NaOH solution. The vessel was incubated at 28° C. with an agitation speed of 1000 rpm and an air flow of 2 liters per minute.

After 72 hours 2-methylpent-4-enoic acid (0.8 ml) was added and the fermentation maintained for a further 72 hours. The mycelium was recovered by filtration and suspended in acetone (500 ml) for 1 hour before filtering. The solid was re-suspended in acetone (500 ml) for 0.5 hour and filtered. The combined filtrates were evaporated to dryness under vacuum to yield a dark coloured oil (8.1 g). This material was partially purified by column chromatography on silica gel (Kieselgel 60, 230–400 mesh, Merck - trademark, 240 g) eluting with a mixture of dichloromethane and ethyl acetate (4:1), collecting 50 ml fractions. These were analysed by t.l.c. and those fractions containing the title compound were combined and evaporated under vacuum. This material was further purified by column chromatography on silica gel (130 g) eluting with mixtures of dichloromethane and diethyl ether initially 4:1 then 2:1 and finally with diethyl ether alone. Fractions rich in the desired product were combined, evaporated to dryness under vacuum and dissolved in methanol (3 ml). This solution was purified by HPLC using a Dynamax 60-A C-18 (Trademark, Rainin) column (41×250 mm) eluting with a mixture of methanol and water (4:1) at a flow rate of 52 ml per minute. Fractions were collected at 3–5 minute intervals and analysed by HPLC. Those containing the desired product were combined and evaporated under vacuum. Final purification was achieved by HPLC using an Ultrasphere-ODS (5 μm) (Trademark—Beckman) HPLC column (10×250 mm) eluting with a mixture of water and methanol (18:82) at a flow rate of 3 ml per minute. Appropriate fractions were combined and evaporated under vacuum to give a white powder identical in all respects to the product of Example 4.

EXAMPLE 6

The procedures of Examples 2 and 3 are repeated except that the substrates listed below are used in place of 2-methyl butyric acid. In each instance, the corresponding milbemycin $A_3$ and $B_2$ derivatives of formula (II) ($R^4=H$ and $CH_3$) are obtained.

| Substrate | $R^2$ |
| --- | --- |
| 2-methylvaleric acid | pent-2-yl |
| 1-cyclohexene carboxylic acid | cyclohexen-1-yl |
| thiophene-2-carboxylic acid | thien-2-yl |
| 3-furoic acid | 3-furyl |
| cyclobutane carboxylic acid | cyclobutyl |
| cyclopentane carboxylic acid | cyclopentyl |
| cyclohexane carboxylic acid | cyclohexyl |
| cycloheptane carboxylic acid | cycloheptyl |
| 3-cyclohexene-1-carboxylic acid | cyclohex-3-enyl |
| 2-methylpent-2-enoic acid | 2-penten-2-yl |
| 2-furoic acid | 2-furyl |
| 5-methylthiophene-2-carboxylic acid | 5-methylthien-2-yl |
| 1-methylcyclopropane carboxylic acid | 1-methylcyclopropyl |
| cyclopropane carboxylic acid | cyclopropyl |
| 2-methylcyclopropane carboxylic acid | 2-methylcyclopropyl |
| 2-methyl-4-methoxybutyric acid | 4-methoxybut-2-yl |
| tetrahydrothiophene-3-carboxylic acid | tetrahydrothien-3-yl |
| 3-methylcyclobutane carboxylic acid | 3-methylcyclobutyl |
| 3-methylene cyclobutane carboxylic acid | 3-methylenecyclobutyl |
| 2-methyl-4-methylthiobutanoic acid | 4-methylthiobut-2-yl |
| tetrahydrothiopyran-4-carboxylic acid | tetrahydrothiopyran-4-yl |
| 3-cyclopentenemethanol | cyclopent-3-enyl |

EXAMPLE 7

The procedure of Example 5 is followed except that the following substrates are used in place of 2-methylpent-4-enoic acid to produce formula (II) compounds wherein $R^4$ is H and $R^2$ is as listed below.

| Substrate | R² |
|---|---|
| thiophene-3-carboxylic acid | thien-3-yl |
| hydroxymethylcyclopentane | cyclopentyl |
| 3-thiophene carboxaldehyde | thien-3-yl |
| 3-cyclohexylpropionic acid | cyclohexyl |
| 3-cyclopentylpropionic acid | cyclopentyl |
| hydroxymethylcyclobutane | cyclobutyl |
| 3-cyclopentyl-1-propanol | cyclopentyl |
| cyclobutylmethylamine | cyclobutyl |
| ethyl cyclobutanecarboxylate | cyclobutyl |
| 2-(cyclobutylcarbonyl)propionic acid | cyclobutyl |
| ethyl 2-(3-thiophenecarbonyl)propionate | thien-3-yl |
| 1-methylcyclopropane carboxylic acid | 1-methylcyclopropyl |
| 2,3-dimethylbutyric | 1,2-dimethylpropyl |
| 2-methylhexanoic acid | hex-2-yl |
| 2-cyclopropyl propionic acid | 1-cyclopropylethyl |
| 4-methylenecyclohexane carboxylic acid | 4-methylenecyclohexyl |
| 3-methylcyclohexane carboxylic acid (cis/trans) | 2-methylcyclohexyl |
| 1-cyclopentene carboxylic acid | cyclopenten-1-yl |
| tetrahydropyran-4-carboxylic acid | tetrahydropyran-4-yl |
| 2-chlorothiophene-4-carboxylic acid | 2-chlorothien-4-yl |
| (S)-2-methylpentanoic acid | (S)-pent-2-yl |
| (R)-2-methylpentanoic acid | (R)-pent-2-yl |

EXAMPLE 8

Anthelmintic Activity

Anthelmintic activity was evaluated against *Caenorhabditis elegans* using the in vitro screening test described by K. G. Simpkin and G. L. Coles in Parasitology, 1979, 79, 19. The product of Examples 1 and 2 killed 100% of the worms at a well concentration of 0.01 parts per million.

EXAMPLE 9

Insecticidal Activity

Activity against the larval stage of the blowfly *Lucilia cuprina* (Q strain) is demonstrated using a standard procedure in which first instar larvae are kept in contact with filter paper treated with test compound. The test compound is first applied to the paper as an acetone solution. The treated filter papers are then placed into tubes containing 1 ml of newborn calf serum and the first instars are added. The product of Examples 1 and 2 killed 100% of the larvae when applied to the filter paper at a level of 10 milligrams per square meter.

We claim:

1. A process for producing a compound of the formula

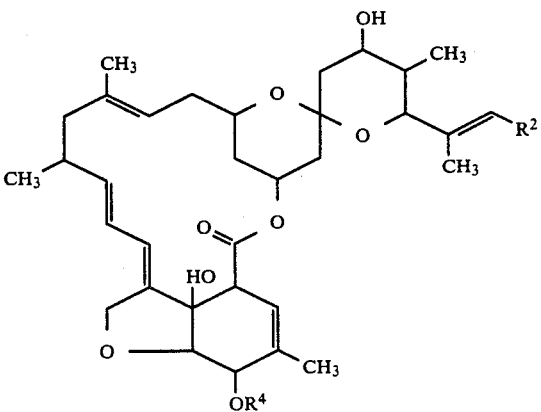

wherein

R² is a $C_3$–$C_8$ straight or branched-chain alkyl, alkenyl or alkynyl group which may optionally contain an oxygen or sulphur atom as part of the chain, or a $C_3$–$C_8$ cycloalkyl or cycloalkenyl group, or a 3 to 6 membered oxygen or sulphur containing heterocyclic ring which may be saturated or fully or partially unsaturated and which may optionally be substituted by one or more $C_1$–$C_4$ alkyl groups or halogen atoms; and R⁴ is hydrogen or methyl; with the proviso that, when R² is branched chain alkyl, it is not isopropyl or 2-butyl, which process comprises aerobically fermenting a strain of the milbemycin producing organism *Streptomyces cyaneogriseus* subsp. *noncyanogenus* NRRL 15773 or *Streptomyces thermoarchaensis* NCIB 12015 in the presence of an aqueous nutrient medium comprising an assimilable source of carbon, nitrogen and inorganic salts and a carboxylic acid of the formula $R^2CO_2H$, wherein R² is as defined above, or a salt, ester or amide thereof or oxidative precursor therefor.

2. A process according to claim 1 wherein R² is (1-methylthio)ethyl or 2-pent-4-enyl.

* * * * *